US012690928B1

(12) United States Patent
Hariri et al.

(10) Patent No.: US 12,690,928 B1
(45) Date of Patent: Jul. 28, 2026

(54) HOMING OF A CABLE-DRIVEN SURGICAL TOOL IN A SURGICAL ROBOTIC SYSTEM

(71) Applicant: Verb Surgical Inc., Santa Clara, CA (US)

(72) Inventors: Alireza Hariri, Santa Clara, CA (US); Ali Asadian, Santa Clara, CA (US); Sina Nia Kosari, Santa Clara, CA (US); Haoran Yu, Santa Clara, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

(21) Appl. No.: 19/191,432

(22) Filed: Apr. 28, 2025

Related U.S. Application Data

(63) Continuation of application No. PCT/IB2024/060618, filed on Oct. 28, 2024.

(60) Provisional application No. 63/595,006, filed on Nov. 1, 2023.

(51) Int. Cl.
A61B 34/30 (2016.01)
A61B 17/34 (2006.01)
A61B 34/00 (2016.01)

(52) U.S. Cl.
CPC .......... A61B 34/30 (2016.02); A61B 17/3417 (2013.01); A61B 34/71 (2016.02); A61B 2017/3454 (2013.01); A61B 2034/305 (2016.02)

(58) Field of Classification Search
CPC ..... A61B 34/30; A61B 17/3417; A61B 34/71; A61B 2017/3454; A61B 2034/305
See application file for complete search history.

(56) References Cited

U.S. PATENT DOCUMENTS

| | | | |
|---|---|---|---|
| 2016/0374772 A1 | 12/2016 | Hasegawa et al. | |
| 2017/0020615 A1* | 1/2017 | Koenig ................. | A61B 34/30 |
| 2021/0059777 A1* | 3/2021 | Overmyer .............. | A61B 34/71 |
| 2021/0282876 A1 | 9/2021 | Ergueta Tejerina et al. | |
| 2022/0346893 A1* | 11/2022 | Tschudy ............. | A61B 17/3211 |
| 2023/0094003 A1 | 3/2023 | Connolly et al. | |
| 2024/0238000 A1* | 7/2024 | Kingsley .............. | A61B 17/295 |
| 2024/0252268 A1* | 8/2024 | Loschak ................ | A61B 34/37 |
| 2024/0374332 A1* | 11/2024 | Takahashi .............. | A61B 34/71 |

FOREIGN PATENT DOCUMENTS

| | | | | |
|---|---|---|---|---|
| CN | 110561425 A | * 12/2019 | ............. | B25J 9/161 |
| KR | 20120022521 A | 3/2012 | | |
| KR | 20190112306 A | 10/2019 | | |
| WO | WO-2023162697 A1 | * 8/2023 | ............. | A61B 34/30 |

OTHER PUBLICATIONS

International Search Report and Written Opinion for PCT/IB2024/060618 mailed Oct. 28, 2024.

* cited by examiner

*Primary Examiner* — Timothy P Graves
(74) *Attorney, Agent, or Firm* — Lempia Summerfield Katz LLC

(57) ABSTRACT

For homing a cable-driven instrument of a surgical robotic system, any elongation of the cables is determined by applying pressure to the cables in a known configuration. The actuator positions for homing are then updated to account for any elongation. As a result, more accurate control and operation of the instrument during surgery is provided.

12 Claims, 6 Drawing Sheets

| Surgical Tool 700 | Cables 710 | Actuators 730 |
|---|---|---|
| | Sensors 720 | Processor 740 |
| | | Memory 740 |

FIG. 7

HOMING OF A CABLE-DRIVEN SURGICAL TOOL IN A SURGICAL ROBOTIC SYSTEM

RELATED APPLICATION

The present patent document is a continuation of PCT/IB2024/060618, filed Oct. 28, 2024, which claims the benefit of the filing date under 35 U.S.C. § 119 (e) of Provisional U.S. Patent Application Ser. No. 63/595,006, filed Nov. 1, 2023, which are both hereby incorporated by reference.

FIELD

Embodiments relate to establishing a home or known configuration of a cable-driven surgical tool of a surgical robotic system.

BACKGROUND

Minimally-invasive surgery (MIS), such as laparoscopic surgery, involves techniques intended to reduce tissue damage during a surgical procedure. MIS may be performed with robotic systems that include one or more robotic arms for manipulating surgical tools based on commands from a remote operator. In robotic MIS systems, it may be desirable to establish and maintain high positional accuracy for surgical instruments supported by the robotic arms.

Surgical instruments for the robotic arms may share similar designs, for example, a tool may have an end effector including a robotic wrist and one or more jaws. The end effectors may include tools for grasping, cutting, suturing, among other surgical tasks. A cable system couples the end effector to actuators in a tool drive, which can drive multi-axial motions (e.g., pitch and yaw) of the end effector. For example, four actuators using four cables drive an end effector with a robotic wrist with a pair of jaws.

Ideally, the angle of joints (e.g., wrist or jaws) can be determined knowing the actuator positions where the cables have positive tensions. When the instrument is placed on the robot arm, it is important to know where the wrist joints are, as the starting position. Using factory homing, the actuator positions to home the instrument in a particular configuration are stored so that the actuators are driven to those positions in order to achieve homing of the instrument. However, in reality, after each use cycle, the home position of the actuators may slightly change due to factors such as plastic deformation of the cables and instrument cleaning and sterilization with special solutions. As a result, the factory homing may become inaccurate.

SUMMARY

By way of introduction, the preferred embodiments described below include methods, systems, instructions, and computer readable media for homing a cable-driven instrument of a surgical robotic system. Starting from a previous homing, any elongation of the cables is determined by applying pressure to the cables in a known configuration. The actuator positions for homing are then updated to account for any elongation. As a result, more accurate control and operation of the instrument during surgery is provided.

In a first aspect, a method is provided for homing a cable-driven instrument of a surgical robotic system. The cable-driven instrument is engaged with a tool driver of a surgical robotic arm. After the engaging, motors of the tool driver are positioned at first calibrated positions for a home configuration of the cable-driven instrument. The motors apply tensions to cables of the cable-driven instrument. Any slack in the cables at the home configuration of the cable-driven instrument is removed. The first calibrated positions of the motors are updated based on positions of the motors after applying the tensions to the cables. The cable-driven instrument is controlled in surgery based on the updated first calibrated positions.

In a second aspect, a surgical robotic system is provided for homing. A surgical tool connects by a first number of cables to a respective number of actuators. The surgical tool connects such that actuation of the actuators moves the surgical tool with a fewer number of degrees of freedom than the first number (e.g., four cables used to control three degrees of freedom). First sensors are configured to sense force applied by the actuators. A processor is configured to control the actuators to apply pressures to the cables without movement of the surgical effector. The pressure is sensed by the first sensors. The processor is configured to determine a home position of the actuators for a home position of the surgical tool using the pressures.

In a third aspect, a method is provided for homing a cable-driven instrument of a surgical robotic system. The cable-driven instrument is positioned at a home position. Tension is applied to cables of the cable-driven instrument while at the home position. Elongations of the cables are determined from forces on the cables and positions of actuators operating the cable-driven instrument at two or more configurations having known references. The cable-driven instrument is operated in surgery with control of the actuators accounting for the elongations.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

FIG. 7 is a block diagram of one embodiment of a system for homing a cable-driven robotic surgical instrument.

DETAILED DESCRIPTION

A cable-driven robotic surgical instrument is homed for use in MIS. The homing places the cable driven robotic instrument to a known position such that the cables are taut, and the distal end of the instrument is at the home position. To deal with undesirable cable elongations, the amount of elongation is determined in order to establish updated or corrected actuator positions to provide the homing (i.e., to place the instrument at the home position). The correction places the wrist as close as possible to its factory-set home configuration.

FIGS. 1-5B illustrate one example of a cable-driven robotic surgical instrument and the robotic surgery system for using the instrument. This example is used in the homing method and by the homing system of FIGS. 6 and 7, respectively. Other cable-driven surgical instruments and/or robotic surgery systems may be used.

In general, an end effector including a robotic wrist and one or more jaws may be coupled to actuators through metal cable or wires. The wires may work, for example, in wire pairs where pulling on one wire imparts an opposite force on the other wire of the wire pair, as such the robotic wrist may be an antagonistic robotic wrist. Jaws are used in this example, but other applied surgical robotic instruments may be used. Applied surgical robotic instruments include graspers, forceps, scissors, needle drivers, retractors, pliers, and cautery instruments, among others.

Figure 1:
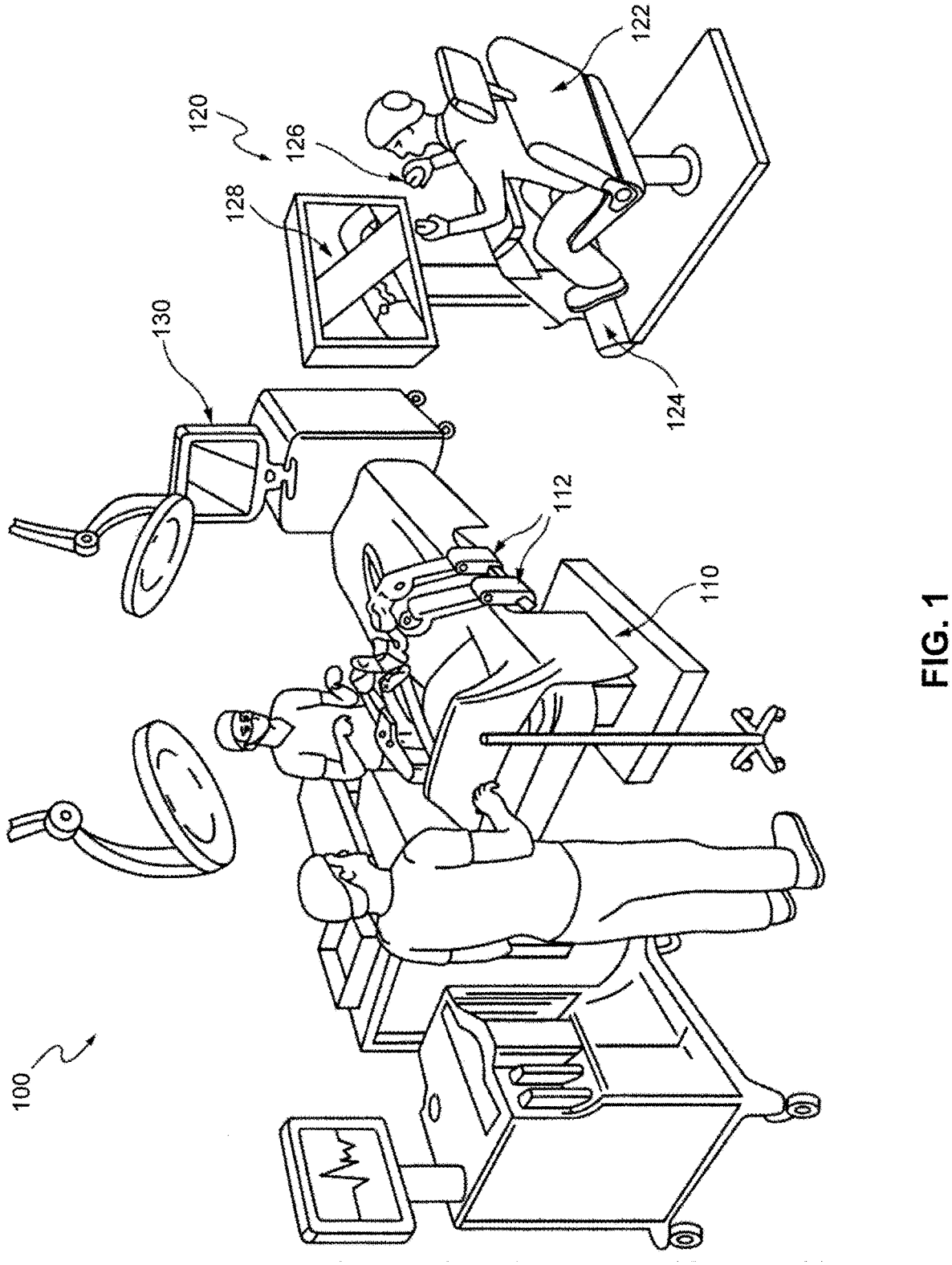
FIG. 1 is a diagram illustrating an example operating room environment with a surgical robotic system, in accordance with aspects of the subject technology.

FIG. 1 is a diagram illustrating an example operating room environment with a surgical robotic system 100, in accordance with aspects of the subject technology. As shown in FIG. 1, the surgical robotic system 100 has a surgeon console 120, a control tower 130, and one or more surgical robotic arms 112 located at a surgical robotic platform 110 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface.

Generally, a user, such as a surgeon or other operator, may use the user console 120 to remotely manipulate the robotic arms 112 and/or surgical instruments (e.g., tele-operation). The user console 120 may be located in the same operation room as the robotic system 100, as shown in FIG. 1. In other environments, the user console 120 may be located in an adjacent or nearby room, or tele-operated from a remote location in a different building, city, or country. The user console 120 may have a seat 122, foot-operated controls 124, one or more handheld user interface devices 126, and at least one user display 128 configured to display, for example, a view of the surgical site inside a patient. As shown in the exemplary user console 120, a surgeon located in the seat 122 and viewing the user display 128 may manipulate the foot-operated controls 124 and/or handheld user interface devices 126 to remotely control the robotic arms 112 and/or surgical instruments mounted to the distal ends of the arms.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 126 held in one hand) and a manual laparoscopic tool. For example, the user's left hand may be manipulating a handheld user interface device 126 to control a robotic surgical component, while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 120 may utilize the foot-operated controls 124 and/or user interface devices 126 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 112. Non-sterile personnel may also be present to assist the surgeon at the user console 120. When the procedure or surgery is completed, the robotic system 100 and/or user console 120 may be configured or set in a state to facilitate one or more post-operative procedures, including but not limited to, robotic system 100 cleaning and/or sterilization, and/or healthcare record entry or printout, whether electronic or hard copy, such as via the user console 120.

In some aspects, the communication between the robotic platform 110 and the user console 120 may be through the control tower 130, which may translate user commands from the user console 120 to robotic control commands and transmit to the robotic platform 110. The control tower 130 may also transmit status and feedback from the robotic platform 110 back to the user console 120. The connections between the robotic platform 110, the user console 120 and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room as well as remote displays accessible via the Internet or other networks. The video output or feed may also be encrypted to ensure privacy and all or portions of the video output may be saved to a server or electronic healthcare record system.

Figures 2, 3A, 3B:
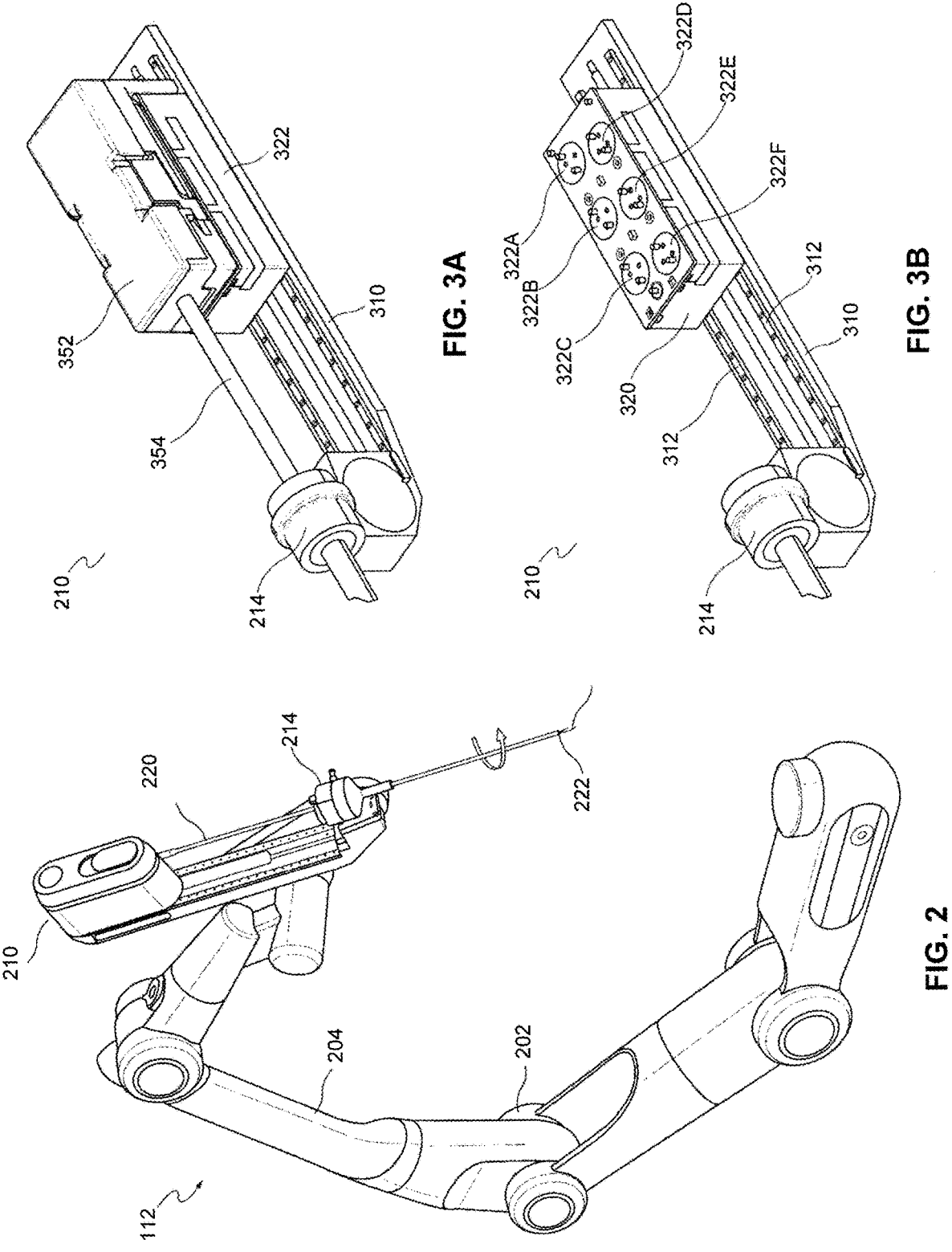
FIG. 2 is a schematic diagram illustrating one exemplary design of a robotic arm, a tool drive, and a cannula loaded with a robotic surgical tool, in accordance with aspects of the subject technology.
FIGS. 3A and 3B are schematic diagrams illustrating an exemplary tool drive with and without a loaded tool adjacent, respectively, in accordance with aspects of the subject technology.

FIG. 2 is a schematic diagram illustrating one exemplary design of a robotic arm, a tool drive, and a cannula loaded with a robotic surgical tool, in accordance with aspects of the subject technology. As shown in FIG. 2, the example surgical robotic arm 112 may include a plurality of links (e.g., a link 204) and a plurality of actuated joint modules (e.g., a joint 202) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 112. The tool drive 210 may include a cannula 214 coupled to its end to receive and guide a surgical instrument 220 (e.g., endoscopes, staplers, grippers, etc.). The surgical instrument (or "tool") 220 may include an end effector 222 at the distal end of the tool. The plurality of the joint modules of the robotic arm 112 can be actuated to position and orient the tool drive 210, which actuates the end effector 222 for robotic surgeries.

FIGS. 3A and 3B are schematic diagrams illustrating an exemplary tool drive with and without a loaded tool adjacent, respectively, in accordance with aspects of the subject technology. As shown in FIGS. 3A and 3B, in one variation, the tool drive 210 may include an elongated base (or "stage") 310 having longitudinal tracks 312 and a tool carriage 320, which is slidingly engaged with the longitudinal tracks 312. The stage 310 may be configured to couple to the distal end of a robotic arm such that articulation of the robotic arm positions and/or orients the tool drive 210 in space. Additionally, the tool carriage 320 may be configured to receive a tool base 352 of the tool 220, which may also include a tool shaft 354 extending from the tool base 352 and through the cannula 214, with the end effector 222 (not shown) disposed at the distal end.

Additionally, the tool carriage 320 may actuate a set of articulated movements of the end effector, such as through a cable system or wires (the terms "cable" and "wire" are used interchangeably) manipulated and controlled by actuated drives (the terms "actuators," "motors," and "drives" are used interchangeably) The tool carriage 320 may include different configurations of actuated drives. For example, the rotary axis drives may include a motor with a hollow rotor and a planetary gear transmission at least partially disposed within the hollow rotor. The plurality of rotary axis drives may be arranged in any suitable manner. For example, the tool carriage 320 may include six rotary drives 322A-322F arranged in two rows, extending longitudinally along the base that are slightly staggered to reduce width of the carriage and increase the compact nature of the tool drive. As clearly shown in FIGS. 3B, rotary drives 322A, 322B, and 322C may be generally arranged in a first row, while rotary drives 322D, 322E, and 322F may be generally arranged in a second row that is slightly longitudinally offset from the first row.

Figures 4A, 4B:
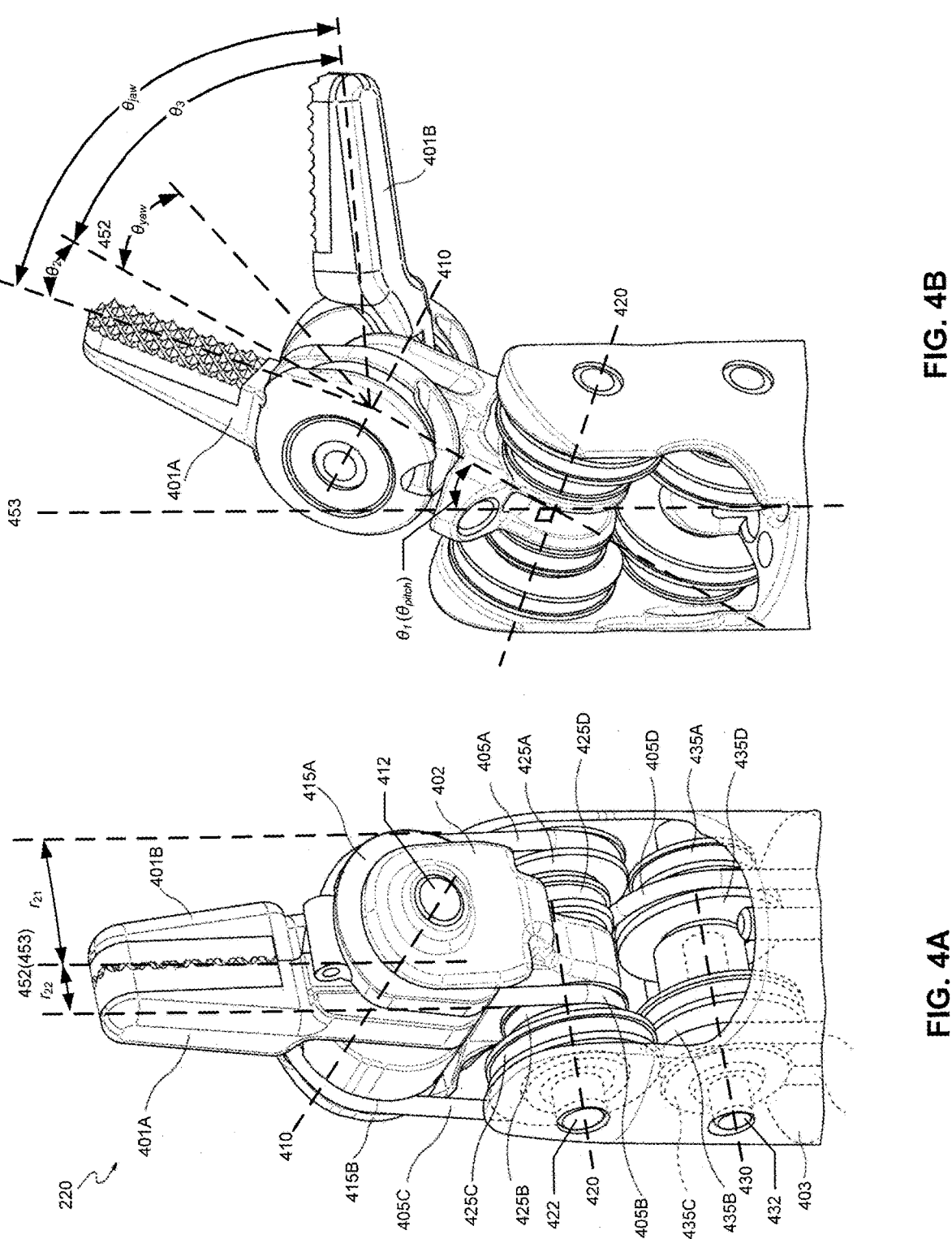
FIGS. 4A and 4B are schematic diagrams illustrating the end effector of an exemplary grasper having a robotic wrist, a pair of opposing jaws, and a pulley and cable system for coupling the robotic wrist and the pair of jaws to the actuators of a tool drive, in accordance with aspects of the subject technology.

FIGS. 4A and 4B are schematic diagrams illustrating an end effector of an exemplary grasper 220 having a robotic wrist, a pair of opposing jaws, and a pulley and cable system for coupling the robotic wrist and the pair of jaws to actuators of a tool drive, in accordance with aspects of the subject technology. Note that although the following tool model and controller design are described with reference to the exemplary surgical robotic grasper, the proposed homing may be adapted to any tools that include an end effector coupled to a tool shaft where cables are used to control the end effector. Similar tools include, but not limited to, graspers, grippers, forceps, needle drivers, retractors, and cautery instruments. Any number of wrist joints, such as one shown in FIGS. 4A and 4B, none, two, or more may be used. Any number of corresponding cables to control the end effector may be used, such as one, two, three, four, or more. In the example of FIGS. 4A and 4B, four cables are used to control three degrees of freedom of the end effector.

As shown in FIG. 4A, the pair of opposing jaws 401A and 401B are movably coupled to a first yoke 402 of the robotic wrist via an extended axle 412 along a first axis 410. The first yoke 402 may be movably coupled to a second yoke 403 of the robotic wrist via a second extended axle 422 along a second axis 420. The pair of jaws 401A and 401B may each be coupled or integrally formed with pulleys 415A and 415B respectively, via the extended axle 412, so that both jaws can rotate about the axis 410. Pulleys 425A, 425B, 425C and 425D are coupled to the extended axle 422 and rotate around the axis 420. The pulleys 425A, 425B, 425C and 425D are arranged into a first set of pulleys 425B and 425C on one side of the yoke 402 and a second set of pulleys 425A and 425D on the other side of the yoke 402. The pulleys 425A and 42C are outer pulleys and the pulleys 425B and 425D are inner pulleys. Similarly, the third set of pulleys 435A, 435B, 435C and 435D are coupled to a third extended axle 432 and rotate around the axis 430, which is parallel to the axis 420.

The grasper 220 can be actuated to move one or both of the jaws 401A and 401B in a variety of ways around the axis 410. For example, the jaws 401A and 401B may open and close relative to each other. The jaws 401A and 401B may also be actuated to rotate together as a pair to provide a yaw motion of the grasper 220. In addition, the first yoke 402, the pulleys 415A and 415B, and the jaws 401A and 401B can rotate about the axis 420 to provide a pitch motion of the grasper 220. These motions of the robotic wrist and/or the jaws of the tool can be effected by controlling four independent cables 405A-405D. As shown in FIG. 4A, cable 405A may start (or terminates) from one side of the pulley 415A and route along pulleys 425A and 435A, and cable 405B is configured to terminate at the other side of the pulleys 415A and route through pulleys 425B and 435B. Similarly, another pair of cables 405C and 405D can be coupled to the jaw 401B. For example, cable 405C extends from one side of the pulley 415B to pulleys 425C and 435C; and cable 405D routes through pulleys 425D and 435D and terminates at the other side of pulley 415B. The third set of pulleys 435A, 435B, 435C and 435D are arranged in such a way as to keep the cables 405A-405D affixing to the second set of pulleys 425A-425D and prevent the cables from slipping or sliding relative to the pulleys 425A-425D.

Controlling the motions of the grasper 220 via four independent cables has several advantages. One advantage may be the reduction of the number of cables that extend from the tool base 352 to the robotic wrist compared to typical on-market designs using six cables (or three cable loops with six cable ends). Less number of cables can reduce the tool size as well as complexity of the wrist assembly, which may benefit minimally-invasive surgical procedures or non-surgical applications. Furthermore, arrangement of four independent cable instead of two or three cable loops not only allows independent control of the tension on each cable without the need for pre-tensioning of the cables, but also enables variable compliance in the wrist joints and increased sensitivity to external loads. Additionally, it is possible to readjust tension on each cable independently, which can further increase tool performance.

As shown in FIGS. 4A and 4B, the grasper 220 can be actuated to move the jaws 401A and 401B in a variety of ways, such as grasping (e.g., jaws rotating independently about axis 410), yaw (e.g., jaws rotating together about axis 410), and pitch (e.g., jaws rotating about axis 420) (three degrees of freedom) by imparting motion to one or more of the pulleys 415A, 415B, 425A, 425B, 425C, and 425D to thereby impart motion on the first yoke 402 and/or one or both of the jaws 401A and 401B. Cables 405A-405D can be grouped into two antagonistic pairs, that is, when one cable of the antagonistic pair is actuated or tensioned, while the other cable is loosened, the jaw will rotate in one direction. Whereas when only the other cable is tensioned, the jaw will rotate in an opposite direction.

For example, cables 405A and 405B are the first antagonistic pair for moving jaw 401A, and cables 405C and 405D are the second antagonistic pair for controlling jaw 401B. When cable 405A is tensioned (e.g., by at least one of the rotary drives 322a-322f) while cable 405B is loosened, jaw 401A closes (moving towards the opposite jaw 401B). On the other hand, when cable 405B is tensioned and cable 405A is loosened, jaw 401A opens (moving away from the opposite jaw 401B). Similarly, when tensioned, cable 405C closes jaw 401B (moving towards the opposite jaw 401A) and cable 405D opens jaw 401B (moving away from the opposite jaw 401A) while the other cable loosens. As another example, grip force between the jaw 401A and jaw 401B can be achieved by continuing to tension both cable 405A and cable 405C (while cable 405B and cable 405D are loosened) after the jaws are closed (touching each other).

In cases when both cables of an antagonistic pair are tensioned at the same time while both cables of the other pair are loosened, the pulley 415A or pulley 415B do not rotate. Instead, the first yoke 402 together with the jaws 401A and 401B are imparted by the pulleys 415A and 415B to pitch about the axis 420. For example, when the pair of cables 405A and 405B are both tensioned simultaneously while the pair of cable 405C and 405D are loosened, the jaws (together with the yoke 402) pitch out of the plane of the paper. Whereas when both cables 405C and 405D are tensioned simultaneously and the pair 405A and 405B are kept loose, the jaws pitch into the plane of the paper.

FIG. 4B is a schematic diagram illustrating example angle definitions for various motions of the grasper 220, in accordance with aspects of the subject technology. The angles are defined in reference to axes 410 and 420, as well as an axis 452 of the first yoke 402 and an axis 453 of the second yoke 403. For example, as shown in FIG. 4B, an angle ($\theta_1$) between axis 452 and the axis 453 may represent the rotation angle of the yoke 402 around axis 420, which may also be defined as the pitch angle ($\theta_{pitch}$) of the grasper 220 (while in FIG. 4A, the axis 452 of the yoke 402 is superimposed over the axis 453 of the yoke 403 because the jaws are staying in the reference position, i.e., no pitch motions). In addition, angles ($\theta_2$) and ($\theta_3$) can represent the angles between each of the jaws 401A and 401B and the axis 452 of the yoke 402 (as the origin), respectively. To differentiate the sides of the axis 452, angles ($\theta_2$) and ($\theta3$) may take on different signs. For example, angle ($\theta2$) is negative and angle ($\theta_3$) is positive, as illustrated in FIG. 4B.

In order to perform control tasks, it is often beneficial to define a consistent coordinate frame for the joint angles. For example, the jaw angle ($\theta_{jaw}$) is the angle between the two jaws 401A and 401B, and the yaw angle ($\theta_{yaw}$) is the angle between the axis 452 and the line bisecting the jaw angle. Therefore:

$$\left( \begin{array}{c} \theta_{pitch} = \theta_1 \\ \theta_{yaw} = \dfrac{1}{2(\theta_1 + \theta_2)} \\ \theta_{jaw} = \theta_2 - \theta_2 \end{array} \right) \tag{1}$$

The transformation between angles in FIG. 4B and the newly defined angles are as follows:

$$\begin{bmatrix} \theta_{pitch} \\ \theta_{yaw} \\ \theta_{jaw} \end{bmatrix} = \begin{bmatrix} 1 & 0 & 0 \\ 0 & 1/2 & 1/2 \\ 0 & 1 & -1 \end{bmatrix} \cdot \begin{bmatrix} \theta_1 \\ \theta_2 \\ \theta_3 \end{bmatrix} \tag{2}$$

Furthermore, the following nomenclature can be established for pulley geometries:

a) $r_{11}$ is the radius of the outer pulleys 425A and 425C on which cables 405A and 405C are residing, respectively;
  b) $r_{12}$ is the radius of the inner pulleys 425B and 425D on which cables 405B and 405D are residing, respectively ($r_{11}$ may or may not be equal to $r_{12}$);
  c) $r_{21}$ is the radius of pulley 415A on the side that cable 405A is residing (with reference to the center of pulley 415A and axle 412 as shown in FIG. 4A);
  d) $r_{22}$ is the radius of pulley 415A on the side that cable 405B is residing (with reference to the center of pulley 415A and axle 412 as shown in FIG. 4A);
  e) $r_{31}$ is the radius of pulley 415B on the side that cable 405C is residing; and
  f) $r_{32}$ is the radius of pulley 415B on the side that cable 405D is residing.

While the above example has symmetrical design, $r_{31}=r_{21}$, $r_{32}=r_{22}$, and $r_{21}=r_{22}$ (as shown in FIG. 4A), in some other designs it is possible to have $r_{31}=r_{21}=r_{32}=r_{22}$, as wells as $r_{11}=r_{12}$. A non-symmetrical design may be used.

The fundamental equation that relates cable tensions ($\xi_{[4\times1]}$) to joint torques ($\tau_{[3\times1]}$) is presented by:

$$\tau_{[3\times1]}=B_{[3\times4]}\cdot\xi_{[4\times1]} \tag{3}$$

where matrix (B) has the following form:

$$B = \begin{bmatrix} -r_{21} & -r_{12} & r_{11} & r_{12} \\ -r_{21} & r_{22} & 0 & 0 \\ 0 & 0 & r_{31} & -r_{32} \end{bmatrix} \tag{4}$$

and ($\xi_1$, $\xi_2$, $\xi_3$, $\xi_4$) corresponds to cable tensions on cables 405A, 405B, 405C and 405D, respectively.

$$\xi_{[4\times1]} = [\xi_1\xi_1\xi_3\xi_4]^T \tag{5}$$

In Eq. (1), ($\tau_{[3\times1]}$) is the vector of virtual joint torques applied by the cables, which may cause the joints to overcome friction and move against the external forces. Vector ($\tau_{[3\times1]}$) has three components:

$$T_{[3\times1]} = [T_1T_2T_3]^T \tag{6}$$

where ($\tau_1$) is the pitch joint torque, and ($\tau_2$) and ($\tau_3$) are the joint torques of jaw 401A and jaw 401B, respectively.

The kinematic relationship that relates the ideal cable displacements (assuming no cable elasticity) and jaw angles are as follows:

$$q_{[4\times1]}[q_1q_2q_3q_4]^T = B^T \cdot \theta_{[3\times1]} \tag{7}$$

where $(q_{[4\times1]})$ is the four-element vector containing the ideal displacements of cables 405A-405D, and $(\theta_{[3\times1]})$ is the vector of angles illustrated in FIG. 4B:

$$\theta_{[3\times1]} = [\theta_1\theta_2\theta_3]^T \tag{8}$$

In the actual case, where the cables are elastic, the actual and ideal cable displacements are related as follows:

$$\xi_{[4\times1]}k_e(x_{[4\times1]} - B^T \cdot \theta_{[3\times1]}) \tag{9}$$

where $k_e$ is the elastic constant of the cables in N/m (assuming all cables are similar).

Angular position and grip force of a distal end effector of a robotic surgical instrument is controlled. The end effector may include a robotic wrist and a pair of opposing members (e.g., jaws or claws), each being movable between an open position and a closed position actuated by two antagonistic wires. A total of four wires may each be driven by independent actuators or motors, as illustrated in FIGS. 3 and 4. The control system may include feedback loops involving position and/or velocity feedback from the actuators and force feedback measured on the four wires, to effect desired position and grip force. In some implementations, the actuator controllers may be running a position plus feedforward current mode. For example, a position controller may drive the distal end effector to the desired angular position in space based on the positional feedback, while a grip force controller provides additional feedforward current based on the grip force measured by load cells on the four wires to achieve the desired grip force between the opposing members or jaws 401A-B.

Figure 5A:
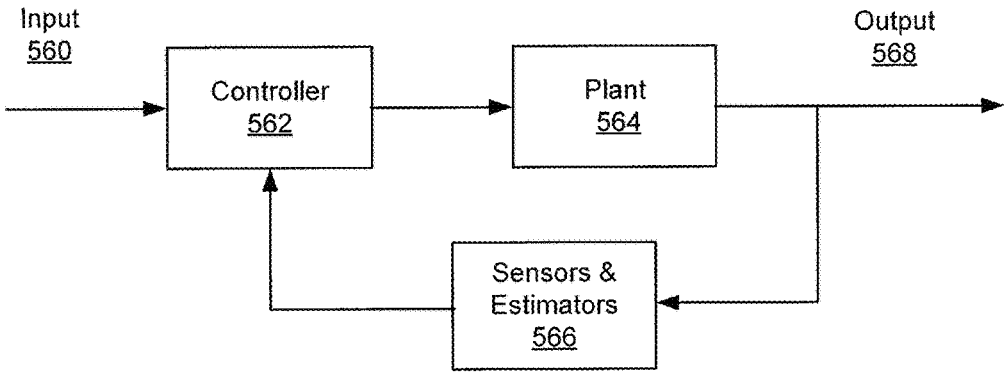
FIGS. 5A and 5B are block diagrams illustrating exemplary control systems for controlling the position and grip force of an end effector of a robotic surgical tool, in accordance with aspects of the subject technology.

FIG. 5A is a block diagram illustrating a high-level control system for controlling a surgical tool. The control system includes an input 560, a controller 562, a plant 564, an output 568, and sensors and estimators 566 on a feedback path between the output 568 and the controller 562. The plant 564 may include tool actuators and end effector (e.g., actuator units 510 and cable and wrist links 512 in FIG. 5B). The controller 562 may include one or more processors configured by software instructions stored on a memory to calculate motions of the plant 564 in response to the input 560, which may indicate a desired movement of the surgical tool's end effector. Commands thus generated by the controller 562 may drive the tool actuators to facilitate the desired movement of the end effector. The output 568, such as position, velocity, cable tension, and/or grip force of the end effector, may be directly measured or estimated by the sensors and estimators 566 and fed back to the controller 562 for closed-loop control.

Figure 5B:
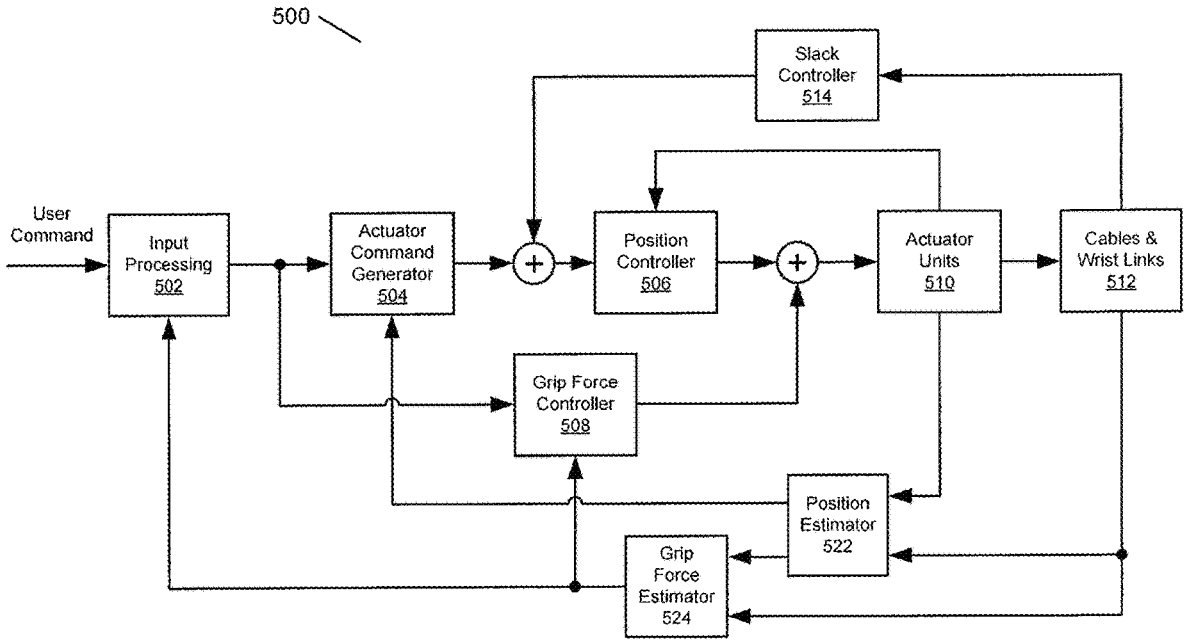

FIG. 5B is a block diagram illustrating an exemplary control system 500 for controlling the position and grip force of an end effector of a robotic surgical tool. The robotic control system 500 has an input processing unit 502, an actuator command generator 504, a position controller 506, a grip force controller 508, a plant including one or more actuator units 510 and/or cables and wrist links 512, a slack controller 514, a position estimator 522, and a grip force estimator 524. Note that additional, different or fewer components than shown in the figure may be used. Variations in the arrangement and types of the components may also be made.

The input processing unit 502 and the actuator command generator 504 receive desired angular positions of the end effector and translate the desired angular positions into corresponding actuator position commands (via inverse kinematics algorithm) and/or grip force command, which are output to the position controller 506 and/or grip force controller 508. For example, the input desired angular positions may include pitch angle $(\theta_{pitch})$, yaw angle $(\theta_{yaw})$, and jaw angle $(\theta_{jaw})$. The desired jaw angle input may be treated as position control command when the angle is no less than a threshold. The threshold corresponds to an angle at which both jaws are just simultaneously in contact with the object(s) in between. In case there is no objects to grasp, the threshold is zero degree when the jaws begin to touch each other. For any desired jaw angle less than the threshold, the input may be translated to a desired grip force command and forwarded to the grip force controller 508, which can generate a current command in addition to the position commands to achieve the desired grip force. For further control and operation, see U.S. Pat. No. 10,166,082.

Figure 6:
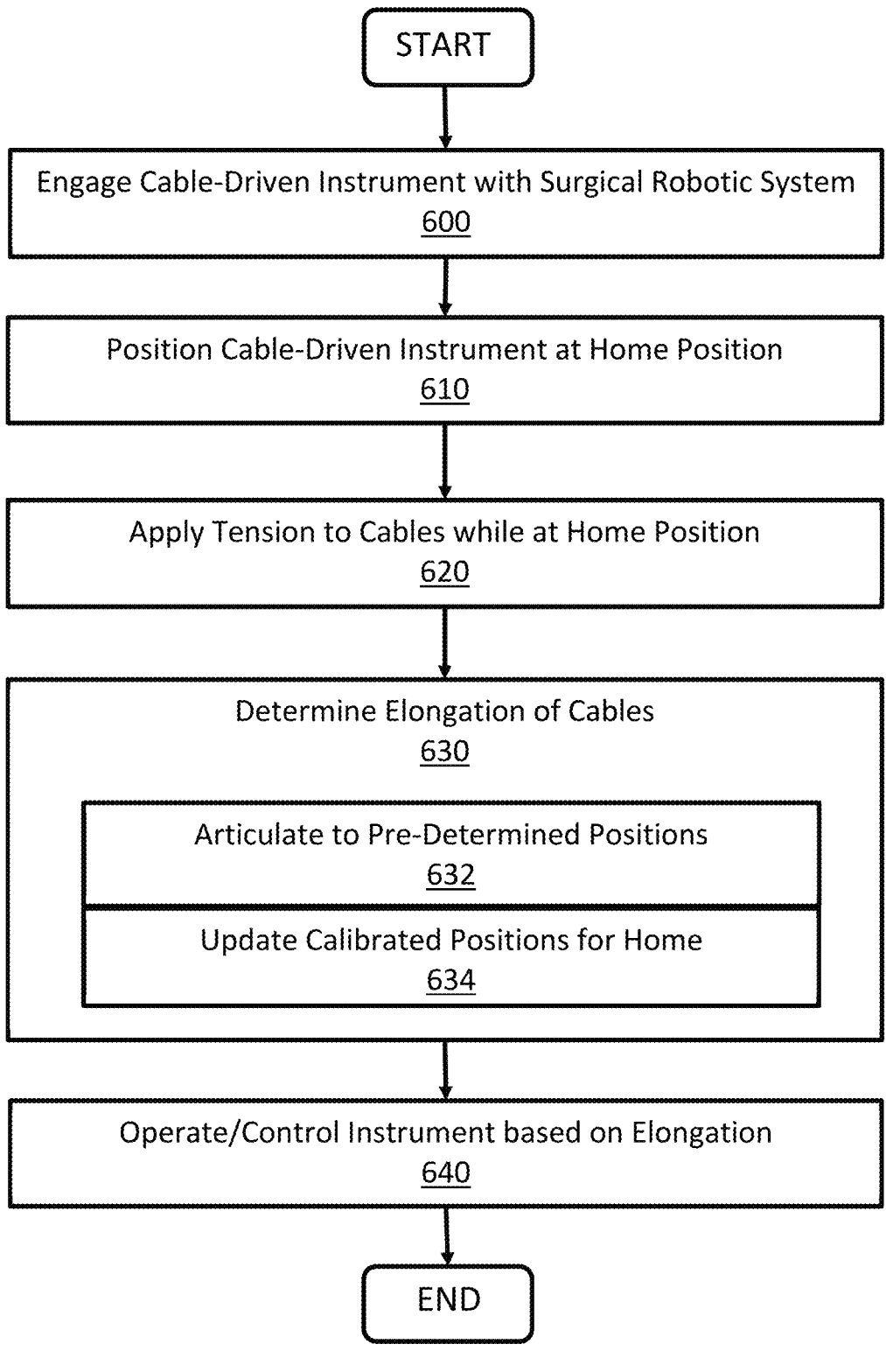
FIG. 6 is a flow diagram of one embodiment of a method for homing a cable-driven instrument of a surgical robotic system.

FIG. 6 shows one embodiment of a method for homing a cable-driven instrument 220 of a surgical robotic system. Homing configures the surgical instrument at a pre-determined pose so that the operator can provide relative changes during surgery. The engaged motors are moved to calibrated positions to place the instrument at the home configuration. To deal with cable elongation resulting in the calibrated motor positions being off, tension is applied to the cables at one or more known locations to determine any offset or adjustment for the motor positions.

The method is performed by the surgical robotic system of FIG. 1, 2, or 3A and 3B or another surgical robotic system. In one embodiment, the surgical robotic system of FIG. 7 performs the method. The method is performed for the surgical instrument of FIGS. 4A and 4B or another instrument. In the example of FIGS. 4A and 4B, four cables control three degrees of freedom for the cable-driven instrument. Other numbers of cables with equal or lesser numbers of degrees of freedom of the instrument may be used. A programmed processor (also referred to here as processing logic) of the control unit or other controller performs the method upon connecting the surgical tool 220 to the tool drive 210. Once the identity of the surgical tool 220 is determined, the processor performs the homing. A memory may store instructions for the programmed processor to home.

The acts are performed in the order shown or a different order. For example, acts 610 and 620 are performed simultaneously. As another example, acts 610-630 are repeated during surgery or for different surgeries. Additional, different, or fewer acts may be provided. For example, act 600 is not provided where engagement previously occurred or is fixed. As another example, act 610 is not provided where the instrument 220 is positioned at another known position than the home position, so act 620 has the tension applied at the other known position. In yet another example, act 640 is not provided. In other examples, acts for arranging the robotic arm 112 for teleoperation, connecting the instrument 220 to the drive 210, and/or surgical use of the engaged and homed instrument 220 are provided.

The process starts once the tool drive 210 is connected with the tool instrument 220. The processor (e.g., controller or control unit) detects engagement of two or more rotary drive pads or discs 322 with a respective two or more rotary tool pads. Using releasable (e.g., spring loaded, physical barrier, or friction fit) fittings, the drive discs 322 mate with the tool discs. The process may start upon detection or after detection of connection and a later occurring initiation event (e.g., user indicates readiness).

In act 600, the cable-driven instrument 220 is engaged with the tool driver 210 of a surgical robotic arm 112. While the tool drive 210 may be connected with the instrument 220, the tool discs may not be engaged with the drive discs 322. The processor controls the engagement. The motors (e.g., actuators) of the tool drive 210 rotate. The rotation of the motors is performed under position control, but other control modes may be used. The drive discs 322 are in frictional contact with the tool discs. The rotation has sufficient force to overcome static friction, so the drive discs 322 rotate relative to the tool discs, which are linked to the surgical tool (e.g., surgical tool 220). The rotation should eventually result in engagement of a physical engagement mechanism (e.g., protrusion and indent, shaped extension and slot, protrusion and stop, and/or snap fit holder and extension) on the tool and drive discs. The fitting relates position of the motors with position of the surgical instrument 220.

Based on one or more monitored motor operating parameters (e.g., current), processing logic detects when the drive disk becomes mechanically engaged with the tool disk. In one embodiment, the detection occurs when or in response to at least one of the one or more motor operating parameters being monitored satisfying a corresponding condition or threshold. The monitored motor operating parameters may correspond with those being controlled by processing logic to cause motion of the motor (e.g., torque, speed.) The processing logic repeatedly checks to see whether or not an engagement condition has been met, e.g., a monitored motor operating parameter has reached a threshold. If so, then a mechanical engagement event is flagged, signifying that the drive disk has mechanically engaged with the corresponding tool disk.

In act 610, the processor positions the cable-driven instrument 220 at a home position. The positioning may not be exact or accurate due to any elongation of the cables 405A-D. After engagement, the motors of the tool driver 210 are positioned at calibrated positions for the home configuration of the cable-driven instrument 220. The motors, in position mode control, are moved to adjust the cables so that the instrument 220 is at a calibrated pose. By positioning the motors using absolute position sensors (e.g., encoders), the cables are adjusted to move the cable-driven instrument 220 into the calibrated pose. For example, FIG. 4A represents the home position or pose for the surgical instrument 220. The motors are rotated to provide the home pose assuming no cable elongation.

In one embodiment, the calibrated positions of the motors are established from a factory calibration. In the factory, when the tool is manufactured, the distal end of the instrument is placed and held at the home position and all the four cables are tensioned to a set tension value (see below in the description for act 620 for some options of control to tension), at which point the positions of the actuators relative to an absolute reference point are stored in the device. All the tool driver motors are commanded (e.g., in position mode) to be positioned at their factory positions stored in the instrument 220. In other embodiments, the calibrated positions are previously updated or set positions based on previous performance of acts 610-630.

In alternative embodiments, the processor controls the motors to position the cable-driven instrument 220 at a hard-limited position. For example, the cable-driven instrument 220 is positioned to apply equal pressure on two jaws against an trocar into which the surgical instrument 220 is placed in preparation for surgical use. The hard-limited position is the home position.

In act 620, the processor controls the motors to apply tension to the cables 405A-D of the cable-driven instrument 220. The motors remove any slack in the cables while at the home configuration of the instrument 220. The application of tension removes slack, including any elasticity, in the transmission (e.g., cables) from the motors to the end effector while at the home position. The processor ensures that the cables 405A-D are taut, so the kinematic link is established between the actuators and the wrist (aka, distal end of the instrument).

The tension is applied equally to the different cables so that the instrument 220 stays at the home position. Any type of control may be used. For example, force or torque control mode is used so that a threshold tension is applied to each cable. In one approach, the motors are operated in a force mode with an outside impedance loop for position. The motors are put in force mode, with an outside impedance loop. A small similar cable tension value (around 5-20 N) is established using the force controllers on the four cables 405A-D. The position control of the outer impedance loop ensures that the wrist position, assuming the factory position is the zero pose, stays at the factory home position. The motors can be commanded in the actuator space or indirectly via the joint space.

In another approach, the motors are operated in a position mode with control by admittance control for force. The application of tension while maintaining pose is achieved using position control mode. Each individual actuator is placed in position mode, and the cable force associated with each motor is regulated via change in the actuator position (admittance control method).

In yet another approach, the threshold tension is applied to all the cables such that the cable-driven instrument 220 is maintained in the home configuration by using null space. Where a greater number of cables and motors (e.g., 4) control a fewer number of degrees of freedom (e.g., 3), control in null space may be used. The actuators are placed in position mode. The actuators are driven in the null space of the wrist until a desired minimum tension is achieved in the cables (e.g., tension equal to factory tensions). The extra cable relative to the degrees of freedom is used to operate the motors to apply tension without changing the pose of the instrument 220.

Other approaches may be used. Any approach applying a threshold tension to each of the cables or transmissions from the motors to the end effector may be used. Where there is slack, the position of the motor for a given cable may change when tension is applied. The change is from the home position and due to elongation.

In act 630, the processor determines any elongations of the cables 405A-D from forces on the cables 405A-D and/or positions of actuators operating the cable-driven instrument 220. For example, the forces establish a threshold tension on the cables 405A-D. The position of the actuators at that threshold tension is sensed, such as with absolution position sensors (e.g., encoders). These positions are the updated or new positions for the home configuration, assuming that the instrument 220 is at the home pose. The difference from the previous position is the elongation. The updated positions are the positions for the home configuration and represent the elongation being determined.

Acts 632 and 634 represent another embodiment. This embodiment provides for more accuracy by not assuming the instrument 220 made it to the home pose using the home positions of the motors prior to applying tension. Additional, different, or fewer acts may be provided to determine the elongation and/or updated calibration.

In act 632, the cable-driven instrument 220 is articulated to one or more pre-determined positions. The instrument 220 is moved to one or more configurations having known references, such as hard limits. The articulation is from the home pose or position. Alternatively, the home pose or position is used as one of the pre-determined positions.

One example pre-determined position is a jaws-closed position, such as shown in FIG. 4A. The pose may be associated with a given amount of force of the jaws against each other, such as a non-zero grip force with the jaws pressing against each other. Any level of force may be used, such as 3-20 N. Another example pre-determined position is a jaws-colliding-with-a-trocar position. For example, without changing an angle of a wrist or joint, the jaws are moved equally to open positions that collide with an enclosure or housing (e.g., trocar into which the surgical instrument 220 has been inserted for surgery).

The position of the actuators and the forces applied at each of the pre-determined positions is used to update the motor positions in act 634. The elongation of the cables may be determined, such as a length or change in length from the motor position when the instrument 220 is at the pre-determined position. A difference from an expected position to the actual position of the motor indicates the elongation.

For homing, this elongation is used to determine a new, corrected, or updated motor position. The elongation is used to update the calibrated positions of the motors. The positions of the motors after applying the tensions to the cables are used to update the calibrated positions of the motors. The calibrated or home positions of the motors to provide the instrument 220 at the home position are updated based on the positions of the motors with the cable-driven instrument 220 at the one or more of the pre-determined positions, such as the jaws-closed position and/or the jaws-colliding-with-a-trocar position.

The determination and update are performed for each of the motors and corresponding cables 405A-D. Elongations for different cables 405A-D may be based on measurements at different ones of the pre-determined positions. Alternatively, multiple measures of elongation for one cable 405 are performed, and the results are averaged.

In one embodiment, articulation to two known configurations in act 632 is used to determine the unknown cable elongations. The first configuration is the jaws at a fully closed position. The jaws are commanded to close until a discernable cable force change (or current spike) is detected. Although, it is important to ensure the jaws are touching, a more robust approach uses the jaws touching with a nonzero gripping force. The second configuration may be achieved via articulation until both jaws collide with a trocar (or another hard obstacle). The collusion is in pitch or yaw directions, but not both. The collision detection is detected from a spike in cable forces or motor currents. In each of these two known configurations, the cable tensions and actuator positions are recorded for use in updating. Differences in actuator position indicate elongation, which may be added to the actuator position used for homing.

In one technique to improve accuracy of the update and corresponding homing, the positions of the motors and force measurements at the pre-determined locations, along with the cable elasticity information, is used to find the elongations of the cables 405A-D. Using the example surgical instrument 220 of FIGS. 4A and 4B with the four cables 405A-D to control the wrist, the motors (e.g., direct current, such as brushless direct current motors) actuate and pull the cables 405A-D. These four cables 405A-D, when pulled, perform the following basic actions with respect to the two jaws: cable 405A closes jaw A (401A), cable 405B opens jaw A (401A), cable 405C closes jaw B (401B), and cable 405D opens jaw B (401B).

The fundamental equation that relates the three joint angles ($\theta$) to four ideal cable movements (q) is as follows:

$$q_{[4\times1]} = B^T_{[4\times3]} \theta_{[3\times1]} \tag{10}$$

Where matrix B has the following form $$B_{[3\times4]} = \begin{bmatrix} -r_{11} & -r_{12} & r_{11} & r_{12} \\ -r_{21} & r_{22} & 0 & 0 \\ 0 & 0 & r_{31} & -r_{32} \end{bmatrix}, \text{ and} \tag{11}$$

q is the movement of cables 405A-D in the ideal case, where the cables 405A-D are rigid. Equation (10) in the expanded form provides movement for each cable 405A-D (cables 1-4) as:

$$q_1 = -r_{11}\theta_1 - r_{21}\theta_2 \tag{12}$$
$$q_2 = -r_{12}\theta_1 + r_{22}\theta_2$$
$$q_3 = +r_{11}\theta_1 + r_{31}\theta_3$$
$$q_4 = +r_{12}\theta_1 - r_{31}\theta_3$$

The processor determines the changes in lengths of the cables 405A-D of the cable-driven instrument 220 from forces on the cables 405A-D at the jaws-closed position with a predetermined non-zero grip force. The elongation is determined for the update based on a relationship given by Hook's law. The cables 405A-D are elastic, and the cable forces and elongation follow Hook's law, which is represented for each cable 405A-D (cables 1-4) as:

$$\xi_1 = k(x_1 - q_1) \tag{13}$$
$$\xi_2 = k(x_2 - q_2)$$
$$\xi_3 = k(x_3 - q_3)$$
$$\xi_4 = k(x_4 - q_4)$$

where k is cable elasticity and x is the actuator displacements. The elasticity k of the cables 405A-D is the same or equal, but different values of k may be used for different cables 405A-D where the elasticity is different. If the cables 405A-D are not assumed to be elastic, the above equations are replaced with a nonlinear equation relating the cable elongation and force.

The undesirable (and unknown) permanent cable elongations on the four cables 405A-D (cables indexed as 1-4) are $\Delta_1$ to $\Delta_4$. To perform homing, the instrument 220 is loaded or connected to the tool driver 210 and the motors are engaged with the instrument 220 in act 600. In act 610, the actuators are then driven to their factory or previously established home position. In act 620, the instrument 220 is positioned in a jaws-closed pre-determined position. To ensure the jaws 401A-B are touching each other, minimum tension and force control is used. A small amount of grip force (e.g., 3 N) is applied by tensioning the cables 405A-D. In this case, the four cable forces of $\xi_1$ to $\xi_4$ are established in the cables. Using the equation set (13), the forces for the four cables 405A-D are:

$$\xi_1 = k(x_{1t} - \Delta_1 - q_1) \tag{14}$$
$$\xi_2 = k(x_{2t} - \Delta_2 - q_2)$$
$$\xi_3 = k(x_{3t} - \Delta_3 - q_3)$$
$$\xi_4 = k(x_{4t} - \Delta_4 - q_4)$$

where, $x_{1t}$ to $x_{4t}$ are actuator movements with respect to the factory home positions, and $q_1$ to $q_4$ are caused by undesired wrist motions (and are unknown). If the wrist stays motionless in pitch and yaw directions while the jaw closure operation is performed (i.e. the wrist stays at home), $q_1$ to $q_4$ will be zero and $\Delta_1$ to $\Delta_4$ may be directly obtained from equation (14). However, this may not be the case.

Where the motions are not zero, some assumptions may be used to solve for the changes in length $\Delta_1$ to $\Delta_4$. For example, an angle of one jaw 401A is equal to an angle of another jaw 401B in the jaws-closed position where the jaws are touching. In this case:

$$\theta_2 = \theta_3 \tag{15}$$

As another example, movement of one jaw 401A is of equal magnitude and opposite direction to a movement of the other jaw 401B. From equation (14), this relationship provides:

$$q_1 = -q_3$$
$$q_2 = -q_4 \tag{16}$$

This in turn can be used in eq. (14) to obtain:

$$\xi_1 = k(x_{1t} - \Delta_1 - q_1) \tag{17}$$
$$\xi_2 = k(x_{2t} - \Delta_2 - q_2)$$
$$\xi_3 = k(x_{3t} - \Delta_3 + q_1)$$
$$\xi_4 = k(x_{4t} - \Delta_4 + q_2)$$

Eliminating $q_1$ and $q_2$ from these equations results in:

$$\Delta_1 + \Delta_3 = x_{1t} + x_{3t} - \xi_1/k - \xi_3/k$$
$$\Delta_2 + \Delta_4 = x_{2t} + x_{4t} - \xi_2/k - \xi_4/k \tag{18}$$

Based on an assumption that the changes in the lengths of the cables 405A and 405C for closing the jaws 401A-B are equal and the changes in the lengths of the cables 405B and 405D for opening the jaws 401A-B are equal, the sums from equation 18 may be divided by 2. The divisions provide the resulting changes in length $\Delta_{1-4}$. A similar approach may be used to determine the same elongations using another predetermined position, such as the jaws-in-collusion-with-trocar position.

The processor uses the elongations to change the calibrated positions of the motors to account for elongation of cables 405A-D of the cable-driven instrument 220. For each cable 405A-D and corresponding motor, the respective elongation is added to the previous calibrated position of the motor. The actuators are commanded in position mode to go to the factory or previous position plus the elongation values, which results are the updated calibration or home position for the motors.

In act 640, the surgical robotic system operates the cable-driven instrument 220 in surgery. For example, movements of the user interface devices 126 and/or foot pedals 124 are translated into joint commands, such as with inverse kinematics. The actuators are moved and controlled in a way that accounts for the elongations. The updated calibration positions of the motors, or home positions, are used so that the joint commands to move the motors operates the instrument 220 in the desired manner. The cable-driven instrument 220 is moved in surgery based on the updated calibrated positions of the motors as engaged. From or relative to the home position, an angle of a joint of the cable-driven instrument 220 is changed. Alternatively or additionally, the jaws are opened or closed. The amount of movement or opening and closing is controlled, in part, by the difference from the updated position.

Figure 7:
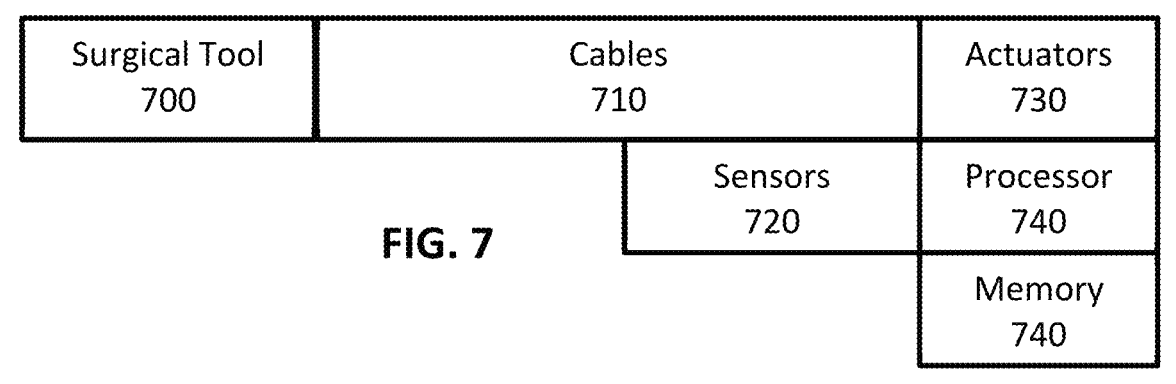

FIG. 7 is a block diagram representing a surgical robotic system according to one embodiment. The system may be, for example, the system of FIGS. 1-3B. The system uses a surgical tool 700, such as disclosed in FIGS. 4A and 4B. The surgical robotic system is used for homing that accounts for cable elongation and/or transmission deformation, such as implementing the method of FIG. 6.

The surgical tool 700 connects through cables 710 to actuators 730 (e.g., motors) when engaged. Sensors 720, such as force sensors (e.g., load cells) and/or position sensors (e.g., encoders for absolute position), are used to control and/or determine elongation. The processor 740, using instructions in the non-transitory computer readable storage medium 750, controls operation of the actuators 730 using information from the sensors 720.

The surgical tool 700 is a grasper with two jaws but may be another type of surgical instrument. The surgical tool 700 connects by a number of cables 710 to a respective number of actuators 730, such as four cables connecting with four engaged actuators 730. The cables 710 allow for actuation of the actuators 730 to move the surgical tool 700, such as opening and closing jaws and/or rotating in pitch and/or yaw. In one embodiment, the actuation moves the surgical tool 700 in a fewer number of degrees of freedom than there are cables 710. For example, the surgical tool has a jaw with a wrist so has three degrees of freedom controlled by four cables 710 and corresponding actuators 730.

The sensors 720 are configured to sense force and/or position. For example, the sensors 720 are force sensors, such as strain gauges, on the cables 710 or shafts of the actuators 730. Alternatively, force is sensed by current draw by the actuators 730. The forces applied by the actuators 730 to the cables 710 and/or tool 700 are sensed. As another example, the sensors 720 are position sensors, such as absolute position encoders, on the actuators 730.

The processor 740 is a general processor, application specific integrated circuit, field programmable gate array, digital signal processor, controller, digital circuit, analog circuit, combinations thereof, and/or other now known or later developed processor for robotics control. The processor 740 is configured by software, hardware, and/or firmware to home the actuators 730 and surgical tool 700.

The processor 740 is configured to engage the surgical tool 700 with the actuators 730, control the actuators 730 to configure the surgical tool 700 in a home configuration once engaged (e.g., control the actuators 730 to move to home positions), and then apply pressures along the cables 710. For example, the processor 740 controls the actuators 730 to apply pressures to the cables 710 without movement of the surgical end effector. The pressure is sensed by the sensors 720 so that a set or threshold amount of pressure is applied to all of the cables 710. In one embodiment, the processor 740 controls the actuators 730 to apply the pressures using operation in the null space provided by a difference between the number of cables and the fewer number of degrees of freedom. The actuators 730 may be controlled to move the tool 700 to one or more pre-determined positions, such as positions associated with hard limits that may be detected without reliance on position of the actuators 730.

The processor 740 is configured to determine a home position of the actuators 730 for a home position of the surgical tool 700 using the pressures. Due to elongation of the cables 710 from usage, cleaning, and/or time, the home positions of the actuators 730 may change over time. The processor 740 is configured to determine the home position of the actuators 730 by operation of the actuators 730 to position the surgical tool in one or more known configurations. Changes in lengths of the cables 710 may be determined from positions of the actuators 730 where the tool 700 is at the known configuration (e.g., jaws closed or jaws at the trocar). The change in length is used to determine and set the home position. For example, for each actuator 730, a difference of a current position and a past position for the tool 700 at a same hard limit location indicates the elongation. This elongation is added to the home position of the actuator 730, resulting in an updated or corrected home position accounting for the change in length of the cable 710.

The processor 740 may be configured to operate the tool 700 during surgery. Using the homing, the position of the tool 700 may be accurately controlled, such as control with respect to the home position. By updating the homing over the life of the tool 700, accurate control may be provided over the life of the tool 700. The tool 700 is used during surgery for a patient based, in part, on the corrected home positions of the actuators 730.

Other Illustrative Embodiments include the following. Illustrative Embodiments for one type of claim (e.g., system, method, computer program, or computer readable storage medium) may be provided in other types (e.g., system as a method). Illustrative Embodiments for one set (e.g., Illustrative Embodiments 1-9) may be used in other sets.

Illustrative Embodiment 1. A method for homing a cable-driven instrument of a surgical robotic system, the method comprising: engaging the cable-driven instrument with a tool driver of a surgical robotic arm; positioning, after the engaging, motors of the tool driver to first calibrated positions for a home configuration of the cable-driven instrument; applying tensions to cables of the cable-driven instrument by the motors, the applying removing any slack in the cables at the home configuration of the cable-driven instrument; updating the first calibrated positions of the motors based on positions of the motors after applying the tensions to the cables; and controlling the cable-driven instrument in surgery based on the updated first calibrated positions.

Illustrative Embodiment 2. The method of Illustrative Embodiment 1 further comprising: articulating the cable-driven instrument to one or more pre-determined positions from the home configuration; wherein updating comprises updating based on positions of the motors with the cable-driven instrument at the one or more pre-determined positions.

Illustrative Embodiment 3. The method of Illustrative Embodiment 2 wherein articulating to the one or more pre-determined positions comprises articulating to a jaws-closed position and a jaws-colliding-with-a-trocar position, and wherein updating comprises updating based on the positions of the motors with the cable-driven instrument at the jaws-closed position and the jaws-colliding-with-a-trocar position.

Illustrative Embodiment 4. The method of any of Illustrative Embodiments 2-3 wherein articulating to the one or more pre-determined positions comprises articulating to a jaws-closed position with a predetermined non-zero grip force, and wherein updating comprises determining changes in lengths of cables of the cable-driven instrument from forces on the cables at the jaws-closed position with the predetermined non-zero grip force.

Illustrative Embodiment 5. The method of Illustrative Embodiment 4 wherein updating comprises updating based on a relationship given by Hook's law.

Illustrative Embodiment 6. The method of any of Illustrative Embodiments 4-5 wherein updating comprises updating based on an angle of a first jaw being equal to an angle of a second jaw in the jaws-closed position and based on a movement of the first jaw being of equal magnitude and opposite direction to a movement of the second jaw.

Illustrative Embodiment 7. The method of any of Illustrative Embodiments 4-6 wherein updating comprises updating based on assumptions that the changes in the lengths of the cables for closing first and second jaws are equal and the changes in the lengths of the cables for opening the first and second jaws are equal.

Illustrative Embodiment 8. The method of any of Illustrative Embodiments 1-7 wherein updating comprises changing the first calibrated positions to account for elongation of cables of the cable-driven instrument.

Illustrative Embodiment 9. The method of any of Illustrative Embodiments 1-8 wherein positioning comprises positioning the motors using position mode control based on absolute position sensors, where the first calibrated positions are from a factory calibration.

Illustrative Embodiment 10. The method of any of Illustrative Embodiments 1-9 wherein applying comprises applying with the motors in a force mode and control by an outside impedance loop for position or with the motors in a position mode and control by admittance control for force.

Illustrative Embodiment 11. The method of any of Illustrative Embodiments 1-10 wherein four cables control three degrees of freedom of the cable-driven instrument, and wherein applying comprises applying a threshold tension by driving the motors in a null space.

Illustrative Embodiment 12. The method of any of Illustrative Embodiments 1-11 wherein applying comprises applying a threshold tension to all the cables such that the cable-driven instrument is maintained in the home configuration.

Illustrative Embodiment 13. The method of any of Illustrative Embodiments 1-12 wherein controlling comprises (1) changing an angle of a joint of the cable-driven instrument and/or (2) opening or closing jaws of the cable-driven instrument with an amount of (1) change or (2) opening or closing controlled by a difference from the updated first calibrated positions.

Illustrative Embodiment 14. A surgical robotic system for homing, the surgical robotic system comprising: a surgical tool connected by a first number of cables to a respective number of actuators, the surgical tool connected such that actuation of the actuators moves the surgical tool with a fewer number of degrees of freedom than the first number; first sensors configured to sense force applied by the actuators; a processor configured to control the actuators to apply pressures to the cables without movement of the surgical effector, the pressure sensed by the first sensors, and the processor configured to determine a home position of the actuators for a home position of the surgical tool using the pressures.

Illustrative Embodiment 15. The surgical robotic system of Illustrative Embodiment 14 wherein the surgical tool comprises a jaw with a wrist, the surgical tool having three degrees of freedom where the first number is four, and wherein the processor is configured to control the actuators to apply the pressures operating in null space provided by a difference between the first number and the fewer number.

Illustrative Embodiment 16. The surgical robotic system of any of Illustrative Embodiments 14-15 wherein the processor is configured to engage the surgical tool with the actuators, control the actuators to configure the surgical tool in a home configuration once engaged, and then apply the pressures.

Illustrative Embodiment 17. The surgical robotic system of any of Illustrative Embodiments 14-16 wherein the processor is configured to determine the home position of the actuators by operation of the actuators to position the surgical tool in one or more known configurations.

Illustrative Embodiment 18. The surgical robotic system of Illustrative Embodiment 17 wherein the processor is configured to determine the home position from a change in length of the cables.

Illustrative Embodiment 19. A method for homing a cable-driven instrument of a surgical robotic system, the method comprising: positioning the cable-driven instrument at a home position; applying tension to cables of the cable-driven instrument while at the home position; determining elongations of the cables from forces on the cables and positions of actuators operating the cable-driven instrument at two or more configurations having known references; and operating the cable-driven instrument in surgery with control of the actuators accounting for the elongations.

Illustrative Embodiment 20. The method of Illustrative Embodiment 19 wherein determining the elongations comprises determining from differences in the positions of the actuators from pre-determined positions and the forces.

The above description of illustrated embodiments of the invention, including what is described below in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize. For example, although FIGS. 4A and 4B depict a surgical tool 220 that has a particular cable-driven transmission, the homing process described above is also applicable to other types of surgical tools having different transmissions (not necessarily cable-driven.) These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for homing a cable-driven instrument of a surgical robotic system, the method comprising:

engaging the cable-driven instrument with a tool driver of a surgical robotic arm;

positioning, after the engaging, motors of the tool driver to first calibrated positions for a home configuration of the cable-driven instrument, the home configuration being a first pose of the cable-driven instrument;

applying tensions to cables of the cable-driven instrument by the motors, the applying removing any slack in the cables at the home configuration of the cable-driven instrument;

articulating the cable-driven instrument to one or more pre-determined positions from the home configuration, wherein articulating to the one or more pre-determined positions comprises articulating to a jaws-closed position with a predetermined non-zero grip force;

updating the first calibrated positions of the motors based on positions of the motors after applying the tensions to the cables, the first calibrated positions as updated designating the home configuration of the cable-driven instrument in the first pose as distinguished from other possible poses, wherein updating comprises:

updating based on positions of the motors with the cable-driven instrument at the one or more pre-determined positions, and determining changes in lengths of cables of the cable-driven instrument from forces on the cables at the jaws-closed position with the predetermined non-zero grip force and based on a relationship given by Hooke's law; and controlling the cable-driven instrument in surgery based on the updated first calibrated positions.

2. The method of claim 1 wherein articulating to the one or more pre-determined positions comprises articulating to a jaws-closed position and a jaws-colliding-with-a-trocar position, and wherein updating comprises updating based on the positions of the motors with the cable-driven instrument at the jaws-closed position and the jaws-colliding-with-a-trocar position.

3. The method of claim 1 wherein updating comprises updating based on an angle of a first jaw being equal to an angle of a second jaw in the jaws-closed position and based on a movement of the first jaw being of equal magnitude and opposite direction to a movement of the second jaw.

4. The method of claim 1 wherein updating comprises updating based on assumptions that the changes in the lengths of the cables for closing first and second jaws are equal and the changes in the lengths of the cables for opening the first and second jaws are equal.

5. The method of claim 1 wherein updating comprises changing the first calibrated positions to account for elongation of cables of the cable-driven instrument.

6. The method of claim 1 wherein positioning comprises positioning the motors using position mode control based on absolute position sensors, where the first calibrated positions are from a factory calibration.

7. The method of claim 1 wherein applying comprises applying with the motors in a force mode and control by an outside impedance loop for position or with the motors in a position mode and control by admittance control for force.

8. The method of claim 1 wherein four cables control three degrees of freedom of the cable-driven instrument, and wherein applying comprises applying a threshold tension by driving the motors in a null space.

9. The method of claim 1 wherein applying comprises applying a threshold tension to all the cables such that the cable-driven instrument is maintained in the home configuration.

10. The method of claim 1 wherein controlling comprises (1) changing an angle of a joint of the cable-driven instrument and/or (2) opening or closing jaws of the cable-driven instrument, with an amount of change in the changing or the opening or the closing controlled by a difference from the updated first calibrated positions.

11. A method for homing a cable-driven instrument of a surgical robotic system, the method comprising:

positioning the cable-driven instrument at a home position at a first pose;

applying tension to cables of the cable-driven instrument while at the home position;

articulating the cable-driven instrument to one or more pre-determined positions from the home configuration, wherein articulating to the one or more pre-determined positions comprises articulating to a jaws-closed position with a predetermined non-zero grip force;

updating the first calibrated positions of actuators based on positions of the actuators after applying the tensions to the cables, the first calibrated positions as updated designating the home configuration of the cable-driven instrument in the first pose as distinguished from other possible poses, wherein updating comprises:

updating based on positions of the actuators with the cable-driven instrument at the one or more pre-determined positions, and determining changes in lengths of cables of the cable-driven instrument from forces on the cables at the jaws-closed position with the predetermined non-zero grip force and based on a relationship given by Hooke's law;

operating the cable-driven instrument in surgery with control of the actuators accounting for the elongations.

12. The method of claim 11 wherein determining the elongations comprises determining from differences in the positions of the actuators from pre-determined positions and the forces.

* * * * *